(12) United States Patent
Slager

(10) Patent No.: US 9,439,892 B2
(45) Date of Patent: Sep. 13, 2016

(54) MACROLIDE PARTICULATES, METHODS FOR PREPARATION, AND MEDICAL DEVICES ASSOCIATED THEREWITH

(71) Applicant: SurModics, Inc., Eden Prairie, MN (US)

(72) Inventor: Joram Slager, Saint Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 14/280,054

(22) Filed: May 16, 2014

(65) Prior Publication Data

US 2014/0343491 A1     Nov. 20, 2014

Related U.S. Application Data

(60) Provisional application No. 61/824,200, filed on May 16, 2013.

(51) Int. Cl.
| | |
|---|---|
| *A61K 9/00* | (2006.01) |
| *A61K 31/436* | (2006.01) |
| *A61K 9/107* | (2006.01) |
| *A61K 9/19* | (2006.01) |

(Continued)

(52) U.S. Cl.
CPC .......... *A61K 31/436* (2013.01); *A61K 9/0019* (2013.01); *A61K 9/1075* (2013.01); *A61K 9/19* (2013.01); *A61K 9/5123* (2013.01); *A61K 9/5138* (2013.01); *A61K 9/5146* (2013.01); *A61L 29/085* (2013.01); *A61L 29/16* (2013.01); *Y10T 428/2982* (2015.01)

(58) Field of Classification Search
None
See application file for complete search history.

(56) References Cited

U.S. PATENT DOCUMENTS

| | | |
|---|---|---|
| 7,232,486 B2 | 6/2007 | Keri et al. |
| 8,048,448 B2 | 11/2011 | Ludwig et al. |

(Continued)

FOREIGN PATENT DOCUMENTS

| | | |
|---|---|---|
| WO | WO 2008/013416 | 1/2008 |
| WO | WO 2008/014222 | 1/2008 |
| WO | WO 2012/026896 | 3/2012 |

OTHER PUBLICATIONS

Kohler, U., et al. (2008) "Investigations on non-Spherical Reference Material Using Laser Diffraction and Dynamic Image Analysis", Particulate Systems Analysis, 1-5.

(Continued)

*Primary Examiner* — Robert A Wax
*Assistant Examiner* — Melissa Mercier
(74) *Attorney, Agent, or Firm* — Kagan Binder, PLLC

(57) ABSTRACT

The disclosure provides macrolide particulates including a macrolide therapeutic agent such as rapamycin at high concentration in the particulate. In one method the particulates are made by adding a composition containing an polyoxyethylene sorbitan n-acyl ester, poly(ethyleneimine), or alkylated quaternary ammonium salt to a composition including macrolide dissolved in an alcohol such as ethanol. In another method the particulates are made by adding a non-solvent composition to a composition including macrolide and an alkyl-substituted chromanol dissolved in an alcohol such as ethanol. The formed macrolide particulates have one or more desirable properties including sizes in the range of 0.1 µm to 10 µm, spherical or near spherical shapes, low polydispersity, and/or stability. The macrolide particulates can be used for therapeutic compositions, or in association with an implantable or insertable medical device, such as associated with a polymeric coating on a device.

14 Claims, 10 Drawing Sheets

Zotarolimus

Everolimus

(51) Int. Cl.
*A61K 9/51* (2006.01)
*A61L 29/08* (2006.01)
*A61L 29/16* (2006.01)

(56) References Cited

U.S. PATENT DOCUMENTS

| | | | |
|---|---|---|---|
| 8,337,733 B2 | 12/2012 | Westedt et al. | |
| 8,585,642 B2 * | 11/2013 | Doshi | A61K 9/127 604/101.04 |
| 8,668,667 B2 | 3/2014 | Chappa | |
| 8,927,000 B2 | 1/2015 | Chappa et al. | |
| 2009/0246252 A1 | 10/2009 | Arps et al. | |
| 2012/0004605 A1 | 1/2012 | Chappa | |
| 2012/0028908 A1 | 2/2012 | Viswanath et al. | |
| 2012/0083733 A1 | 4/2012 | Chappa | |
| 2013/0035483 A1 | 2/2013 | Zeng et al. | |
| 2014/0336571 A1 | 11/2014 | Slager et al. | |

OTHER PUBLICATIONS https://www.sympatec.com/EN/ImageAnalysis/Fundamentals.html, "Fundamentals—Particle Size and Shape Calculation by Image Analysis", Sympatec GmbH System—Partikel-Technik; retrieved Jan. 6, 2016.

* cited by examiner

Zotarolimus

Everolimus

Sirolimus / Rapamycin

Temsirolimus

Pimecrolimus

Tacrolimus

Ridaforolimus / Deforolimus

US 9,439,892 B2

MACROLIDE PARTICULATES, METHODS FOR PREPARATION, AND MEDICAL DEVICES ASSOCIATED THEREWITH

CROSS-REFERENCE TO RELATED APPLICATION

The present non-provisional Application claims the benefit of commonly owned provisional application having Ser. No. 61/824,200, filed on May 16, 2013, entitled MACROLIDE PARTICULATES, METHODS FOR PREPARATION, AND MEDICAL DEVICES ASSOCIATED THEREWITH, which Application is incorporated herein by reference in its entirety.

FIELD

The disclosure relates to a macrolide particulates and methods for their formation. The disclosure also relates to medical devices that are implanted or inserted in the body and associated with the macrolide particulates. The disclosure also relates to treatment methods using composition and medical devices associated with the macrolide particulates.

BACKGROUND

Therapeutic agents can be introduced into a subject by several different routes. Most commonly, therapeutic agents are orally administered because it is a convenient, safe, and cost effective way to make the agent systemically available to the body. However, in many cases, it is desired to deliver therapeutic agent using a route other than oral administration, such as by injection or through use of an insertable or implantable medical device.

Some preparations of therapeutic agent are liquid formulations in which the therapeutic agent is dissolved in an aqueous injection composition and then injected into a subject to provide a therapeutic effect. Other preparations of therapeutic agent can be associated with and released from an insertable or implantable medical device. For example, polymeric coatings for medical devices that include therapeutic agent have been used for the delivery of the therapeutic agent from the coating to a target tissue. In many cases, such coatings are prepared by dissolving the therapeutic agent and polymeric material in a common solvent and applying the composition to a device surface to form a coating. However, technical challenges associated with polymer chemistry, compatibility of the therapeutic agent with the polymer system, and release of the therapeutic agent from the coating following implantation make the preparation of drug-releasing coated devices very challenging.

For example, non-antibiotic macrolides such as rapamycin have been used for the treatment or prevention of various medical disorders. Rapamycin has been used to prevent or minimize tissue response associated with inflammation, fibrosis, and thrombosis, which may be associated with medical device insertion or implantation. Commercially available rapamycin powder can be crushed or ground for micronization, but particulates that are formed can be substantially heterogenous in size and shape, and this technique can also be detrimental to activity. As such, there exist challenges in the art of macrolide particulate preparation and localized or site-specific delivery of macrolide therapeutic.

SUMMARY

The disclosure is directed to macrolide particulates, methods for their preparation, therapeutic compositions that include the particulates, as well as implantable and insertable medical devices that can be associated with the particulates and capable of releasing the macrolide therapeutic in the body. The disclosure is also directed to the use of macrolide particulates for the treatment of a medical condition in a subject, in which the macrolide therapeutic provides a therapeutic effect to a subject, preventively, or for active treatment of a medical condition.

In studies associated with the current disclosure, it has been found that it is desirable to process the manufacturer's preparation of macrolide, such as rapamycin powder, to a more useful form so that therapeutic compositions can be made, such as ones for injection, or association with an insertable or implantable medical device. The studies have also shown that of particular value are preparations of micronized macrolide particulates with high macrolide content and desirable shape and size dispersion properties.

Methods of the disclosure addresses challenges in the art of macrolide particulate preparation and provides improvements for the preparation of macrolide particulates having desirable particle shape, particle morphology, macrolide release and activity, and particle size dispersity. The present disclosure also addresses challenges in the art of localized or site-specific delivery of macrolide therapeutic, and allows for improvements in macrolide therapeutic release and activity. In turn, this can provide improved medical procedures and preventive or active treatment for subjects having particular medical conditions.

Embodiments of the disclosure include methods for preparing macrolide particulates. In a first embodiment for preparing macrolide particulates, the method includes a step of providing a first composition comprising a macrolide therapeutic agent and an alkyl-substituted chromanol dissolved in a liquid selected from the group consisting C1-C4 alcohols. In another step, a mixture is formed by adding a second composition to the first composition, the second composition being a non-solvent, such as an aqueous composition, for the macrolide therapeutic agent. The mixture of the first and second compositions can be agitated to cause the formation of macrolide particulates.

In another (e.g., second) embodiment for preparing macrolide particulates, the method includes a step of providing a first composition comprising a macrolide therapeutic agent dissolved in a liquid selected from the group consisting of C1-C4 alcohols. Next, a mixture is formed by adding a second composition to the first composition, wherein the second composition is a non-solvent for the macrolide therapeutic agent and comprises a component selected from the group consisting of polyoxyethylene sorbitan n-acyl esters, poly(alkyleneimines), and alkylated quaternary ammonium salts. The mixture of the first and second compositions can be agitated to cause the formation of macrolide particulates. Optionally, in this embodiment, the first composition can optionally include an alkyl-substituted chromanol dissolved in a C1-C4 alcohol.

In some cases the macrolide is a "non-antibiotic" macrolide such as rapamycin (sirolimus), fujimycin (tacrolimus), pimecrolimus, zotarolimus, everolimus, temsirolimus, or ridaforolimus/deforolimus.

In some cases the first composition comprises an alkyl-substituted chromanol of Formula I:

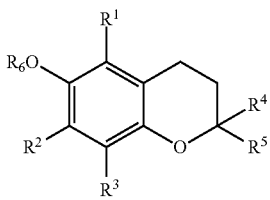

wherein $R^1$, $R^2$, $R^3$, and $R^4$ are independently selected from the group consisting of methyl (—CH$_3$) and hydrogen (—H); $R^5$ is a saturated or partially saturated, linear or branched C4-C16 alkyl group; $R^6$ is selected from the group consisting of —H, —C(O)R$^7$, and —R$^8$(CH$_2$CH$_2$O)$_n$H, wherein $R^7$ is C1-C6 alkyl, and $R^8$ is a covalent bond (—) or a spacer group optionally containing one or more heteroatoms. Compounds of Formula I include those selected from the group consisting of alpha (α) tocopherol, beta (β) tocopherol, gamma (γ) tocopherol, and delta (δ) tocopherol.

Other embodiments of the disclosure are directed to macrolide particulates per se. For example, one embodiment is directed to a macrolide particulates made according to the methods of the disclosure, involving mixing the first and second compositions. In another embodiment, the macrolide particulate comprises a macrolide therapeutic agent in an amount of 95% or greater of the weight of the particulate, and a component selected from the group consisting polyoxyethylene sorbitan n-acyl esters, poly(alkyleneimines), alkylated quaternary ammonium salts, alkyl-substituted chromanols, or combinations thereof, wherein the particulate has a spherical or substantially spherical substantially spherical shape.

The macrolide particulates formed according to methods of the disclosure have many desirable properties. First, the macrolide particulate can be formed without having to add a substantial amount of excipient compound. This can ensure that the macrolide particulate preparations have a high activity per weight of the preparation. This can be important in many therapeutic methods, as the amount of macrolide therapeutic that is available to a subject following administration of the macrolide particulates can be maximized. This is also advantageous for applications involving the site-specific delivery of macrolide therapeutic, or the delivery of macrolide therapeutic to a limited access region in the body.

It was also discovered that after a considerable period of storage, the particulates still maintained the same or similar desirable shape and non-aggregation properties observed after the particulates were initially formed.

Another embodiment is directed to a set of particulates comprising a plurality of macrolide particulates. The macrolide particulate set comprises a plurality of macrolide particulates comprising macrolide therapeutic agent in an amount of 95% or greater of the weight of the particulate, a component selected from the group consisting of polyoxyethylene sorbitan n-acyl esters, poly(alkyleneimines), alkylated quaternary ammonium salts, and alkyl-substituted chromanols in an amount in the range of 0.1 to 5% (wt) in the particulate, wherein the particulates in the set have a spherical or substantially spherical shape and a diameter in the range of 0.1 mm to 10 mm. The set of particulates can also have low size dispersity (i.e., a low polydispersity value).

A set of particulates having a low polydispersity tends to have fewer particulate in the set of a size that considerably deviate from the mean particulate size of the set. A low polydispersity can be particularly desirable for drug delivery applications including injectable compositions and implantable medical devices as they can improve composition or device preparation, as well as release of the macrolide therapeutic to the body.

Low polydispersity can be also advantageous for releasing the macrolide therapeutic in a more controlled manner after the particulates have been introduced in the body. For example, a macrolide particulate set with a low degree of polydispersity can be used to prepare a macrolide particulate-containing coating, which has uniform coating properties, and which can release the macrolide therapeutic in a more predictable manner in the body.

Other embodiments of the disclosure are directed to therapeutic compositions and medical devices having a macrolide particulate or set of macrolide particulates. Compositions and devices including the macrolide particulates can be used in drug delivery methods wherein the macrolide is a therapeutic agent. For example, the macrolide particulates can be introduced into a subject by injection, or can be used in a delivery system that modulates release of the macrolide. In some aspects, the macrolide particulates are used to deliver macrolide therapeutic at an intravascular location. In some embodiments, the macrolide particulates are used in association with an implantable or insertable medical device. The macrolide particulates can be associated with the device, in a manner that they are releasable from, immobilized on or within the device, or both.

The macrolide particulates can also be used in conjunction with a polymer system that modulates release of the macrolide therapeutic. The polymer system can be biostable or biodegradable. In some cases the macrolide particulates are associated with a polymeric matrix, and the matrix can be associated with an implantable medical device, such as in a coating on a surface of the device. The macrolide particulates can also be immobilized in an in-situ formed body of polymeric material (such as a crosslinked hydrogel).

In many aspects, the macrolide particulates can be placed within the body where they dissolve and the macrolide therapeutic can be released, providing a therapeutic effect to a subject. The particulates can be introduced into the body alone, or in combination with another component that can modulate release of the macrolide therapeutic. The particulates can be used in therapies so the macrolide therapeutic exerts a site-specific effect, or alternatively, a more general systemic therapeutic throughout the body.

DETAILED DESCRIPTION

Figure 1A:
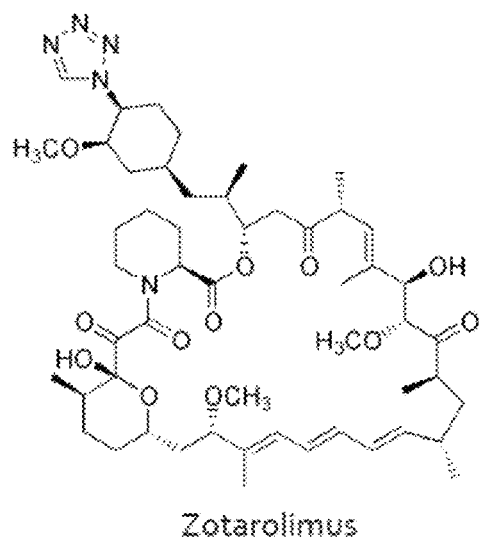
FIGS. 1A-G illustrate chemical structures of various non-antibiotic macrolides.
Figure 1B:
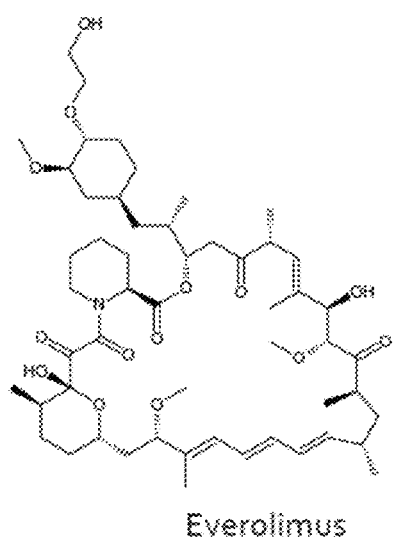
Figure 1C:
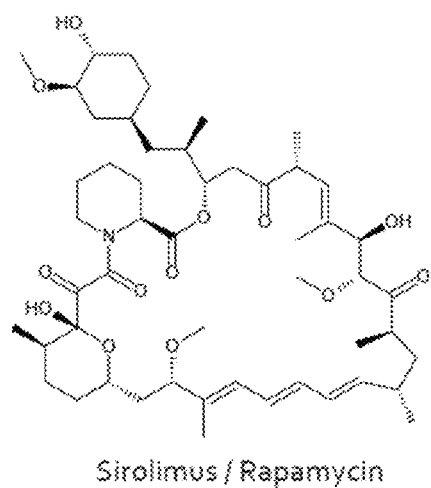
Figure 1D:
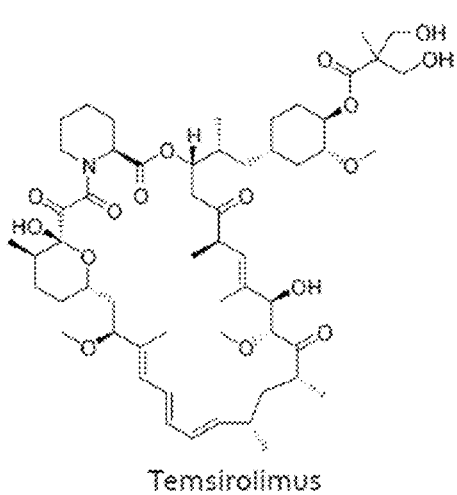
Figure 1E:
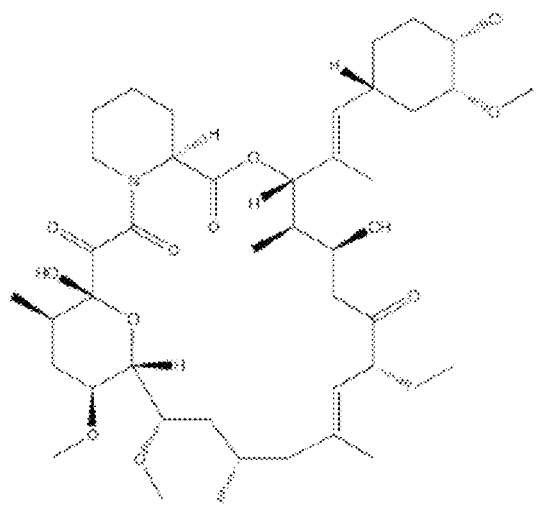
Figure 1F:
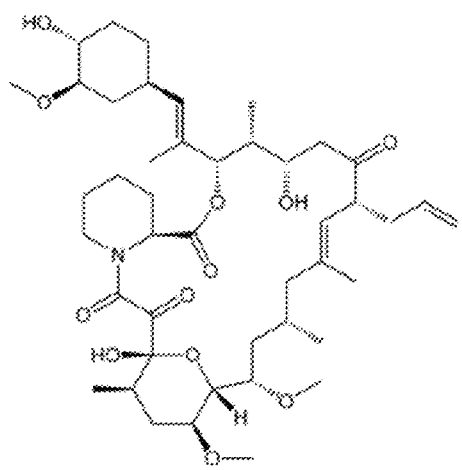
Figure 1G:
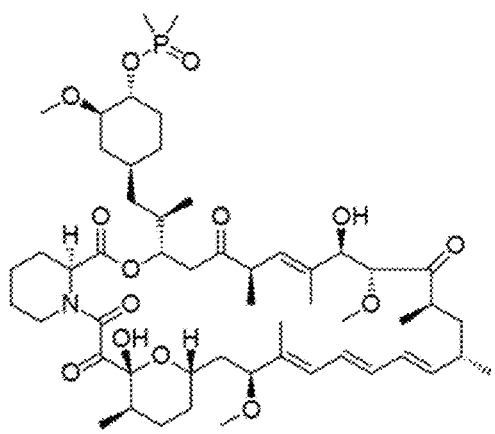

The embodiments of the present disclosure described herein are not intended to be exhaustive or to limit the disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present disclosure provides macrolide particulates, methods for forming these particles, and medical devices having associated macrolide particulates. The processes of the disclosure can also provide "sets" of macrolide particulates with a desirable low degree of dispersity and desirable particulate shapes, with the particulates having high macrolide therapeutic content.

In a treatment method, the macrolide particulates can be placed in a subject, alone or in association with a delivery article or composition, in a manner so the macrolide becomes therapeutically available to the subject. In some more specific delivery approaches, the macrolide particulates are associated with an implantable delivery article for the site-specific release of macrolide therapeutic.

Macrolides are characterized by a large macrocyclic lactone ring, which can be optionally defined by the number of atoms in the ring. The macrocyclic ring includes at least 7 ring atoms selected from carbon, nitrogen, oxygen, sulfur, silicon, phosphorous. Ring atom(s) can optionally be substituted with oxygen, and contain one or more degrees of unsaturation (double or triple bonds). Macrolide compounds of the disclosure can include those that are multicyclic, such as bi- or tricyclic. Some macrolides include sugar molecules (e.g., two or more) bonded to the macrocyclic ring. Many macrolides are found as natural products and belong to the polyketide class of secondary metabolites from various prokaryotic and eukaryotic organisms. Many macrolide therapeutics are chemically synthesized derivatives of naturally-occurring macrolides. Use of non-antibiotic macrolides can be desirable for various indications, such as to prevent or minimize tissue response associated with inflammation, fibrosis, and thrombosis.

Non-antibiotic macrolides include rapamycin (e.g., sirolimus, Rapamune™), everolimus (e.g., Zortress™), pimecrolimus, temsirolimus, fujimycin/tacrolimus, deforolimus, zotarolimus, and biolimus. Chemical structures of some non-antibiotic macrolides are shown in FIGS. 1A-G.

Many of the non-antibiotic macrolides, such as rapamycin, have desirable immunosuppressive and antiproliferative properties. Rapamycin can inhibit growth factor- and mitogen-induced proliferation of T lymphocytes when the rapamycin-FKBP12 complex binds to an effector, and arrests the G1 to S transition of the cell cycle.

Rapamycin has a molecular weight of 914.17 and molecular formula: $C_{51}H_{79}NO_{13}$ (see also FIG. 1). It is insoluble in water, but soluble in ethanol (2 mM), methanol (25 mg/ml), DMSO (25 mg/ml), chloroform, (5 mg/ml), ether, acetone and N,N-dimethylformamide. As commercially supplied, rapamycin exists as one isomer (structurally homogeneous) in the solid form as indicated by X-rays whereas in solution there are two conformational isomers (approx. 4:1) which exist in equilibrium.

Figure 2:
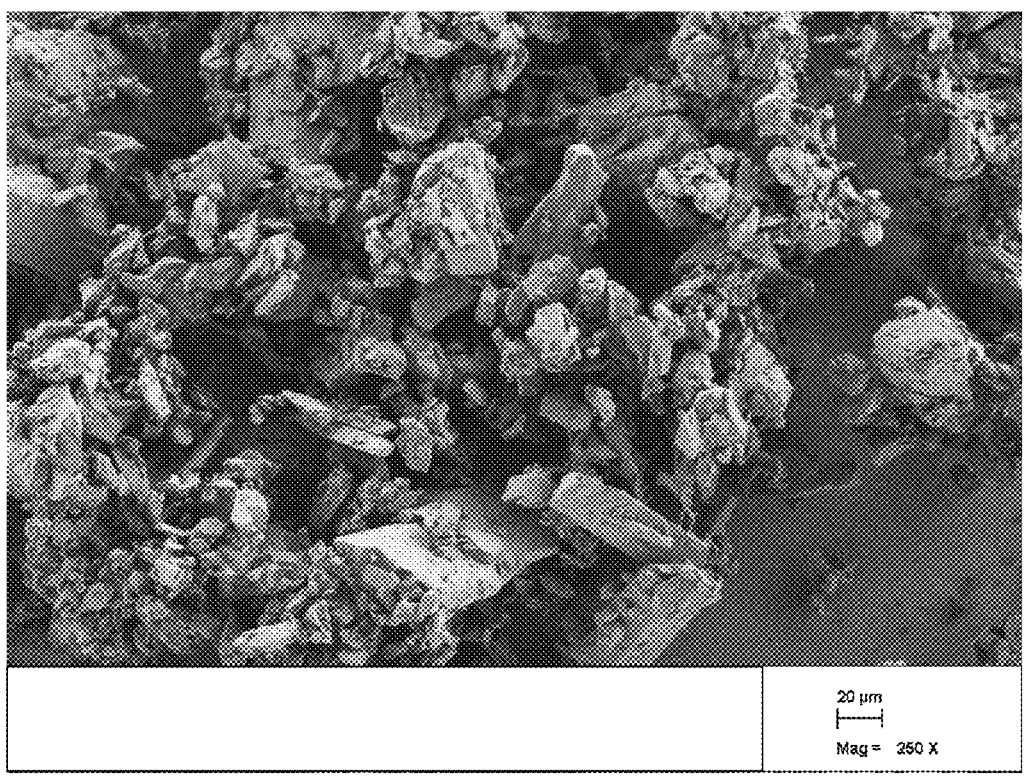
FIG. 2 is an electron micrograph of rapamycin powder from a manufacturer's preparation.
Figure 3A:
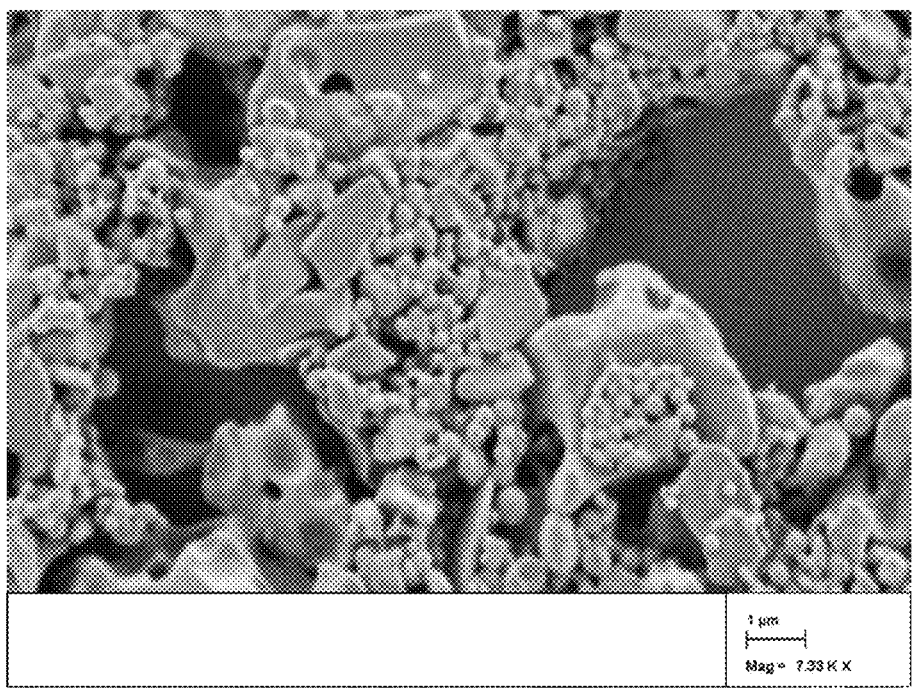
FIG. 3a is an electron micrograph of a rapamycin composition prepared by adding rapamycin/acetone into water.
Figure 3B:
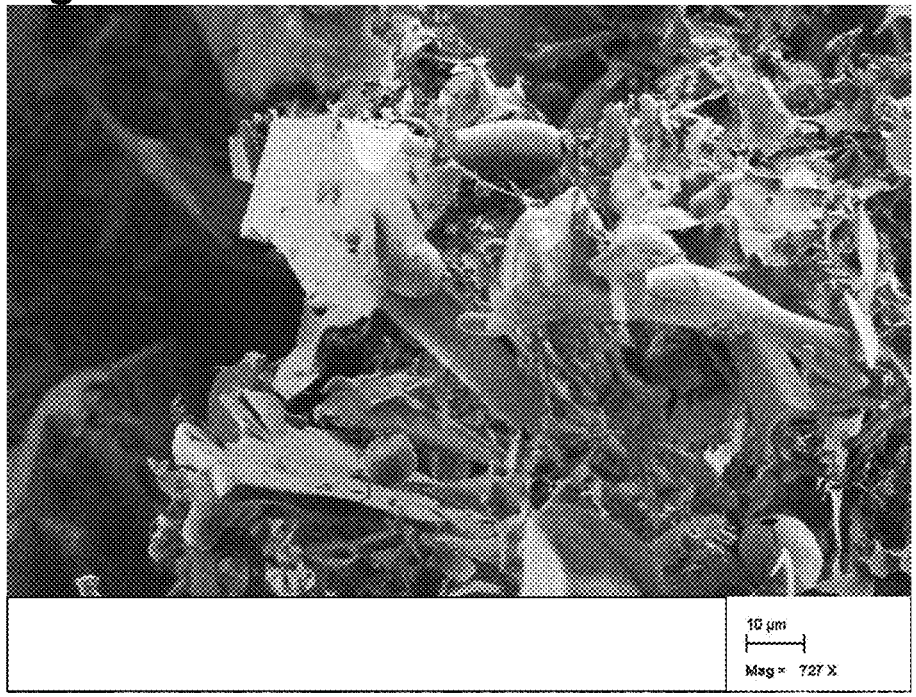
FIG. 3b is an electron micrograph of a rapamycin composition prepared by adding rapamycin/acetone into water, taken after two weeks of dry storage.

Rapamycin is commercially available as a manufacturer's preparation in powdered form (e.g., a "stock composition"). Observed using magnification, the powder can be in the form of flakes having irregular shapes (e.g., jagged outer surfaces) and of various sizes. The sizes of the flakes is rather large, having minimal dimensions of generally greater than about 25 μM, and more typically greater than about 100 μM (see FIG. 2). Stock compositions of rapamycin in powdered form are commercially available from various sources, such as LC Laboratories (Woburn, Mass.) and Sigma Aldrich. Other non-antibiotic macrolides, antibiotic macrolides, and ketolides, are commercially available, or can be prepared using techniques known in the art.

The macrolide compound, such as rapamycin, can optionally be subjected to any purification or enrichment process prior to being used to form the macrolide particulates of the disclosure. Exemplary optional purification or enrichment techniques include one or more affinity, hydrophobic, size exclusion, centrifugal, and liquid chromatographies (such as HPLC).

In embodiments, manufacturer's preparations can be subjected to method steps of the disclosure to transform undesirable irregular shaped and diverse sized macrolide material to more desirable forms useful for compositions and devices delivered to the body. As a general matter, a "first composition" with macrolide therapeutic dissolved in a C1-C4 alcohol, such as ethanol, is prepared. In some embodiments the first composition can include an alkyl-substituted chromanol. Next, a "second composition" that is a non-solvent to the macrolide therapeutic is added to the first composition. In some embodiments the second composition can include a compound having surfactant properties, such as a polyoxyethylene sorbitan n-acyl ester, poly(alkyleneimine), or alkylated quaternary ammonium salt. The second composition is added to the first composition in a manner desirable for promoting the formation of the macrolide particulates.

An initial step in the process of preparing the macrolide particulates involves preparing a liquid composition (e.g., a "first composition") having dissolved therein the macrolide therapeutic. Exemplary liquids (macrolide solvents) in which the macrolide therapeutic can be dissolved include C1-C4 alcohols such as ethanol.

For example, macrolide therapeutic in powdered form from a stock composition can be dissolved in the macrolide solvent. The macrolide solvent can be at any temperature so the macrolide can dissolve in a desired period of time. Upon addition of the macrolide to the macrolide solvent, the composition can be agitated, such as stirred, either manually or mechanically, to increase the rate of dissolution.

The macrolide therapeutic can be dissolved in the macrolide solvent at a concentration sufficient for the formation of macrolide particulates upon addition of the "second" composition. In some modes of practice, the macrolide can be dissolved in the macrolide solvent at a concentration of at least 10 mg/mL, or in the range of about 10 mg/mL to about 100 mg/mL, or more specifically 30 mg/mL to about 70 mg/mL, such as about 50 mg/mL.

In an exemplary mode of practice, rapamycin stock powder can be dissolved in ethanol at 50 mg/mL, at a temperature of about 20° C., with mechanical agitation, such as a stir bar.

In a first embodiment for making the particulates, the first composition having the dissolved macrolide therapeutic also includes an alkyl-substituted chromanol. In some modes of preparation the first composition further includes an alkyl-substituted chromanol of Formula I:

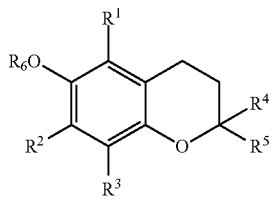

wherein $R^1$, $R^2$, $R^3$, and $R^4$ are independently selected from the group consisting of methyl (—$CH_3$) and hydrogen (—H); $R^5$ is a saturated or partially saturated, linear or branched C4-C16 alkyl group; $R^6$ is selected from the group consisting of H, —C(O)$R^7$, wherein $R^7$ is C1-C6 alkyl, and —$R^8$($CH_2CH_2O$)$_n$H, wherein $R^8$ is a covalent bond (—) or a spacer group optionally containing one or more heteroatoms.

In some embodiments one of $R^1$, $R^2$, or $R^3$ is methyl; in some embodiments at two of $R^1$, $R^2$, and/or $R^3$ are methyl; in some embodiments all of $R^1$, $R^2$, and $R^3$ are methyl.

In some embodiments $R^4$ is methyl (—$CH_3$).

In some embodiments $R^5$ is a saturated branched C4-C16 alkyl group. In some embodiments $R^5$ has the formula:

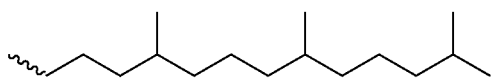

Exemplary compounds of general formula I are tocopherols that include alpha (α) tocopherol:

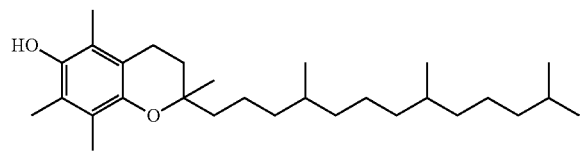

beta (β) tocopherol:

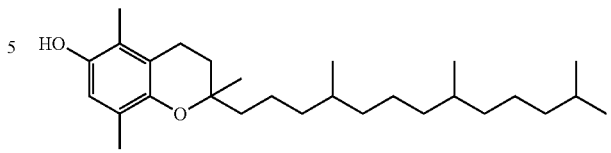

gamma (γ) tocopherol:

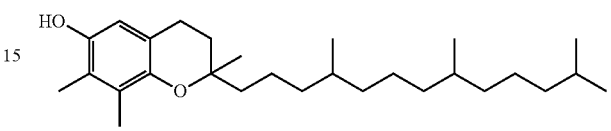

delta (δ) tocopherol:

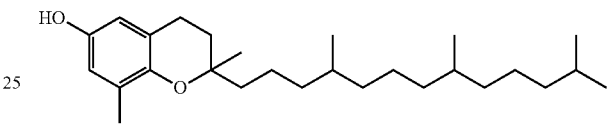

Tocopherols can be commercially obtained from various sources, such as Sigma-Aldrich, St. Louis, Mo.

Also included as compounds of the general formula I are tocotrienols, such as alpha (α) tocotrienol, beta (δ) tocotrienol, gamma (γ) tocotrienols, and delta (δ) tocotrienol. The chemical structure of alpha (α) tocotrienol is shown below:

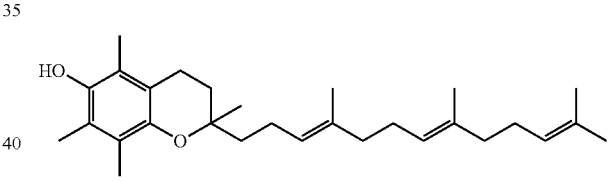

Esters of tocopherols are also contemplated, for example, where $R^6$ is —C(O)$R^7$ wherein $R^7$ is C1-C6 alkyl. An exemplary tocopherol ester is alpha (α) tocopherol acetate:

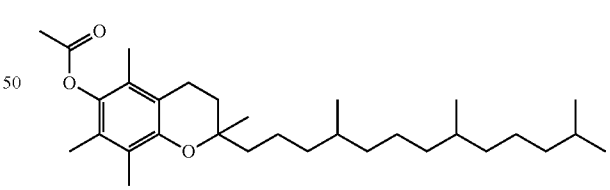

Poly(ethylene glycol) (PEG) derivatives of tocopherols are also contemplated, for example where $R^6$ is —$R^8$($CH_2CH_2O$)$_n$H, and $R^8$ is a covalent bond (—) or a spacer group optionally containing one or more heteroatoms. PEGylated tocopherol/vitamin E derivatives with molecular weights in the range of 2000-5000 Da are commercially available (e.g., from Nanocs, New York, N.Y.).

The alkyl-substituted chromanol can be present in the first composition at a concentration sufficient to promote the formation of macrolide particulates having desirable properties when the second aqueous composition is added to the first composition.

The amount of alkyl-substituted chromanol present in the first composition can be described in various ways, such as in relation to the amount of macrolide therapeutic in the first composition. For example, in some preparations the amount of alkyl-substituted chromanol can be in the range of about 0.001% to about 1.0% (w/w), in the range of about 0.01% to about 0.5% (w/w), or about 0.5% of the amount of macrolide therapeutic in the composition. In some preparations the amount of alkyl-substituted chromanol can be at least 0.01 mg/mL, or in the range of about 0.01 mg/mL to about 10 mg/mL, or 0.1 mg/mL to about 5 mg/mL.

In preparing the first composition, the alkyl-substituted chromanol can be added to the macrolide therapeutic in any suitable matter. In some modes of practice, a concentrated solution of alkyl-substituted chromanol can be dissolved in a solvent miscible with the solvent used to dissolve the macrolide therapeutic, or dissolved in the same solvent used to dissolve the macrolide therapeutic, such as ethanol. Exemplary solvents for preparing a concentrated alkyl-substituted chromanol solution include C1-C4 alcohols, such as ethanol.

The vessel that first composition can be formed in, or eventually is placed in to, can be chosen based on one or more factors, such as a desired amount of macrolide particulates desired to be produced, or the particular method of mixing the first and second compositions. The vessel can be sized to accommodate the amount of second composition added in during the mixing step. In many modes of practice the second composition can be added in a significant volume excess over the first composition, so it can be desirable to use a vessel that holds significantly more liquid than the amount of first composition initially placed into it. For example, the second composition can be added to the first composition in a volume of about at least 10 times the volume of the first composition.

The receptacle can be formed of plastic, glass, or metal, the inner surfaces of which can optionally be treated to minimize or eliminate any non-specific adsorption of the macrolide therapeutic to the surfaces. Exemplary thermoplastics receptacles are fabricated from polypropylene, polystyrene, poly(tetrafluoroethylene) (PTFE), and perfluoroalkoxy (PFA) polymers, such as Teflon™ and Neoflon™.

In a subsequent step in the process of preparing the macrolide particulates, a mixture can be formed by adding to the first composition a second composition. The second composition can be an aqueous composition or a non-solvent liquid to the macrolide therapeutic to form a mixture and then agitating the mixture. For example, the second composition can include heptane as a non-solvent.

In the first embodiment it is not required that the second composition includes a dissolved solid component (such as a surfactant compound), so precipitation of the macrolide therapeutic can be carried out in some cases with a non-solvent such as water or heptane. However, the in the mixing step of the first embodiment, a polyoxyethylene sorbitan n-acyl ester, poly(alkyleneimine), or alkylated quaternary ammonium salt may optionally be included in the second composition.

In the second embodiment it is not required that the first composition includes an excipient component, so the macrolide therapeutic can be dissolved in the C1-C4 alcohol, and then the second composition comprising a polyoxyethylene sorbitan n-acyl ester, poly(ethyleneimine), or alkylated quaternary ammonium salt can be added to the first composition. However, in second embodiment, the first composition can optionally, include the alkyl-substituted chromanol.

Therefore, in some embodiments the second composition comprises polyoxyethylene sorbitan n-acyl ester. Polyoxyalkylene (such as polyoxyethylene) sorbitan n-acyl esters are nonionic surfactants formed by the condensation of sorbitan esters of fatty acids with ethylene oxide (polysorbates), such as sorbitan monooleate with from about 20 to about 60 moles of ethylene oxide. These compounds are commercially available under the tradename of "Tweens™", from, for example, ICI US, Inc. Examplary polysorbates include Polysorbate 20 (polyoxyethylene 20 sorbitan monolaurate, Tween™ 20) and Polysorbate 80 (polyoxyethylene 20 sorbitan monooleate, Tween™ 80).

Exemplary amounts the polyoxyethylene sorbitan n-acyl ester in the second composition can be in the range of about 10 μg/mL to about 100 μg/mL, or more specifically 25 μg/mL to about 75 μg/mL, such as about 50 μg/mL.

In some embodiments the second composition comprises a water soluble poly(alkyleneimine). The water soluble poly(alkyleneimine) can be a compound of general formula II:

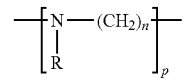

in which R may be a hydrogen atom or a group of formula

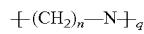

n is an integer between 2 and 10, preferably n is between 2 and 5; and p and q are integers, with the sum of p+q being that the average molecular weight of the polymer is between 100 and $10^7$ Da, preferably between $10^3$ and $10^6$ Da. Formula II includes homopolymers and heteropolymers.

Polyethyleneimine (PEI) and polypropyleneimine (PPI) polymers are exemplary polymers. PEI of various molecular weights, such as 50,000 Da (PE150K) and 800,000 Da (PE1800K), are commercially available.

Exemplary amounts of the poly(alkyleneimine) in the second composition can be at least 0.1% w/w, or in the range of about 0.1% w/w to about 10% w/w, or more specifically 0.25% w/w to about 2.5% w/w, such as about 1% w/w.

In some embodiments the second composition comprises an alkylated quaternary ammonium salt. The alkylated quaternary ammonium salt can be a compound of general formula III:

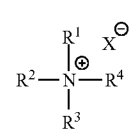

wherein $R^1$, $R^2$, $R^3$, and $R^4$ are independently selected from H and linear, branched, and cyclic alkyl groups, wherein the total number of carbon atoms among $R^1+R^2+R^3+R^4$ is an integer in the range of 6 to 30, or more preferably 10 to 22; and X is a halogen anion. In exemplary embodiments: $R^1$, $R^2$, and $R^3$ are methyl ($-CH_3$) groups; $R^4$ is a linear or branched alkyl group having 10 to 22 carbon atoms, or 12 to 20 carbon atoms.

Exemplary compounds of formula III include cetyltrimethylammonium bromide (CTAB), cetyltrimethylammonium chloride (CTAC), cetyltrimethylammonium hydrosulfate (CTAS), tetradecyltrimethylammonium bromide (TTAB), and octadecyltrimethylammonium bromide (OTAB).

Exemplary amounts the alkylated quaternary ammonium salt in the second composition can be at least 10 μg/mL, in the range of about 10 μg/mL to about 100 μg/mL, or more specifically 25 μg/mL to about 75 μg/mL, such as about 50 μg/mL.

As a general matter, the second composition is added to the first composition to form a mixture. In the step of forming a mixture, the second composition can be added to the first composition with the first composition initially being in volume excess to the added second composition.

In the step of mixing, gradually more of the second composition can be added to the first composition. At a point in the mixing step, the volume of the second composition added can equals the volume of the first composition. After this point, the volume of the second composition added can surpass the volume of the first composition. In many modes of practice the second composition can be added in a volume excess over the first composition. For example, the second composition can be added to the first composition in a volume of at least about 10 times the volume of the first composition, at least about 15 times the volume of the first composition, or at least about 20 times the volume of the first composition. The volume relationship can optionally be described by ratio (vol:vol), with the amount of second composition added to the first composition about 10:1 (vol:vol) or greater, such as in the range of about 15:1 (vol:vol) to about 100:1 (vol:vol), or of about 15:1 (vol:vol) to about 25:1 (vol:vol).

The second composition can be added to the first composition at a desired rate. The rate of addition can be calculated by the following formula:

$$\frac{\text{total amount of second composition added/}}{\text{total amount of second composition added (\%)}}{\text{time}}$$

Mixing can be generally carried out until the first and second compositions are sufficiently combined, which may only take a few seconds, or may be carried out over many minutes. Longer mixing time may be performed for larger volumes. Depending on the factors, such as the type and concentration of the macrolide therapeutic, or the polyoxyethylene sorbitan n-acyl ester, poly(alkyleneimine), alkylated quaternary ammonium salt, or alkyl-substituted chromanol, etc., the mixing step period can be very short (such as about 10 second or less) or may be carried out for many minutes.

During the step of mixing precipitation of the macrolide therapeutic and particulate formation can occur. In some modes of practice, the rate of addition of the second composition to the first composition can vary depending on when the macrolide therapeutic precipitates during mixing. For example, when water (second composition) is added to mixture of rapamycin and alpha (α)-tocopherol (first composition), the water can be slowly added until precipitation of the rapamycin occurs, and then water can be quickly added after this point. In this sense, during the mixing step, the rate of addition of the second composition to the first composition can occur in two or more phases, with the rate of addition being slower in an initial (e.g., first) phase and faster in a later (e.g., second) phase.

Addition of the second composition can be performed with agitation during a portion of, or all of, the addition steps to form the mixture. In some modes of practice, the mixing can be performed with sufficient agitation and in a manner to rapidly mix the first and second compositions. Mixing can be performed to quickly and incrementally increase the volume of liquid to promote particulate formation. The mode of agitation can be chosen based on factors such as the size of the receptacle containing the mixture, and the quantity of particulates desired to be produced. Exemplary agitation techniques include the use of an overhead stirrer, use of stirring equipment such as stir bars, or even by manually shaking the receptacle.

Formation of macrolide particulates can be determined visually, or by other methods, such as by spectrometry. For example, the mixture may be clear at the onset of the addition of the second composition, and then turn very slightly cloudy upon formation of macrolide particulates. However, in some cases, macrolide particulates may be formed even though there is not a distinct visual difference between the first composition (prior to mixing) and the mixture of the first and second compositions. Therefore, in some modes of practice, it may be desirable to monitor formation of macrolide particulates spectrophotometrically. Spectrophotometric measurements may also be useful for determining the optimal conditions for particulate formation.

As a general matter the method of the disclosure can provides macrolide particulates formed predominantly of macrolide therapeutic. Minor or trace amounts of a polyoxyethylene sorbitan n-acyl ester, poly(alkyleneimine), alkylated quaternary ammonium salt, or alkyl-substituted chromanol, or combinations thereof, can be present in the formed macrolide particulates.

A macrolide particulate formed "predominantly" of macrolide therapeutic is a particulate that, by weight, contains more macrolide therapeutic than one, or more than one, other components (compared individually) in the macrolide particulate. To illustrate this, the macrolide particulates of the disclosure include, in the least, a macrolide therapeutic (e.g., component A) and a polyoxyethylene sorbitan n-acyl ester, poly(alkyleneimine), alkylated quaternary ammonium salt, or alkyl-substituted chromanol, or combinations thereof (e.g., component B), wherein the macrolide therapeutic can be present in a greater amount by weight than the polyoxyethylene sorbitan n-acyl ester, poly(alkyleneimine), alkylated quaternary ammonium salt, or alkyl-substituted chromanol, or combinations thereof in the macrolide particulate. Optionally, the macrolide particulate may include other components (for example, components C, D, or E, etc., or combinations thereof). However, if optional components such as C, D, or E, etc., are included each of these optional components individually would be present, by weight, in an amount less than that of the macrolide therapeutic.

Preferably, the formed macrolide particulate comprises an amount of macrolide therapeutic (component A), by weight, of about 90% or greater, such as in the range of about 90% to about 99.99% (range a1), of about 95% or greater, such as in the range of about 95% to about 99.99% (range a2), of about 97.5% or greater, such as in the range of about 97.5% to about 99.99% (range a3), of about 99% or greater, such as in the range of about 99% to about 99.99% (range a4), of about 99.5% or greater, such as in the range of about 99.5% to about 99.99% (range a5). In specific embodiments, component A can be a non-antbiotic macrolide, such as rapamycin, present in an amount in any of ranges a1-a5.

Preferably, the formed macrolide particulate comprises an amount of polyoxyethylene sorbitan n-acyl ester, poly(alkyleneimine), alkylated quaternary ammonium salt, or alkyl-substituted chromanol, or combinations thereof (component B), by weight, of about 10% or less, such as in the range of about 0.01% to about 10% (range b1), of about 5% or less, such as in the range of about 0.01% to about 5% (range b2), of about 2.5% or less, such as in the range of about 0.01% to about 2.5% (range b3), of about 1% or less, such as in the range of about 0.01% to about 1% (range b4), or of about 0.5% or less, such as in the range of about 0.01% to about 0.5% (range b5). In specific embodiments, component B can be selected from the group consisting of alpha (α) tocopherol, beta (β) tocopherol, gamma (γ) tocopherol, and delta (δ) tocopherol, present in an amount in any of ranges b1-b5.

In some embodiments, the formed macrolide particulate comprises macrolide therapeutic, such as rapamycin, and polyoxyethylene sorbitan n-acyl ester, poly(alkyleneimine), alkylated quaternary ammonium salt, or alkyl-substituted chromanol (such as a tocopherol), in range a1 and b1, respectively, range a2 and b2, respectively, range a3 and b3, respectively, range a4 and b4, respectively, or range a5 and b5, respectively (ranges of component A and component B).

The amount of macrolide therapeutic and polyoxyethylene sorbitan n-acyl ester, poly(alkyleneimine), alkylated quaternary ammonium salt, or alkyl-substituted chromanol used in macrolide particulate formation can optionally be expressed as the range of molar ratio between the two. For example, using rapamycin having a MW of 914.2 Da and alpha (α) tocopherol having a MW of 430.7 DA, the ratio of the molar ratio ranges of component A and component B can optionally be expressed as in the range of about 4.5:1 to about 5000:1, about 9.5:1 to about 5000:1, or about 50:1 to about 5000:1, respectively.

Beneficially, the present disclosure shows that sets of macrolide particulates can be formed having desired discrete sizes, those of about 10 μm or less, such as in the range of about 0.1 μm to about 10 μm.

In many aspects, the method of the disclosure produces macrolide particulates that are spherical or substantially spherical in shape. In some cases, because the macrolide particulate can have a spherical or substantially spherical shape, it can be referred to as a macrolide "nanosphere" or macrolide "microsphere," depending on the average size of the spherical particulate of the particulate set. Nanospheres generally refer to those spherical particulates having a size of less than 1 μm, and more typically in the range of about 10 nm to about 500 nm, and microspheres generally refer to those spherical particulates having a size of greater than 1 um, and more typically in the range of about 1 um to about 50 μm.

In a spherical macrolide particulate the distance from the center to the outer surface of the particulate can be about the same for any point on the surface of the particulate. A substantially spherical macrolide particulate may have a difference in radii, but the difference between the smallest radii and the largest radii is generally not greater than about 40% of the smaller radii, and more typically less than about 30%, or less than 20%.

The macrolide particulates of the present disclosure can be delivered to a site within the body for the therapeutic treatment of a medical condition. Generally, when placed in contact with a body fluid macrolide therapeutic in molecular form will be released from the particulate, which can provide a bioactive effect locally or systemically in the body.

In some preparations, the macrolide particulates are prepared to dissolve and release macrolide therapeutic in an aqueous environment, such as body fluid. Optionally, individual macrolide particulates can be provided with a very thin coating (e.g., "shell"), or can be encapsulated to regulate release of the macrolide therapeutic. In some cases, the coating or shell can be in contact with the outer surface of the particulate and have a thickness that is less than the diameter of the macrolide particulate per se. The coating or shell around the particulate may delay the release of the macrolide therapeutic from the particulates after placement within a patient. The coating or capsule can provide a mechanism for the sustained delivery or prolonged release of macrolide therapeutic in a subject.

In some embodiments, the macrolide particulates can be included in a therapeutic liquid delivery composition. The liquid composition can be prepared for the delivery of the macrolide particulates via injection into a target location in the body. For example, the microparticle compositions can be formulated for subcutaneous, intramuscular, intravenous, intrathecal, intraperitoneal, or intraocular injections. The macrolide particulates in the liquid composition can optionally include a coating or can be encapsulated.

In some aspects, the macrolide particulates are associated with a system that controls the release of the macrolide therapeutic to the body. For example, the macrolide particulates can be included within an implantable medical device, such as in an internal reservoir of an implantable medical device. The body can include one or more apertures, or can have a membrane, and macrolide therapeutic can be released from the reservoir exiting the device through the apertures or membrane, upon which it becomes to the tissue or fluid in a subject. Exemplary medical devices having apertures capable of releasing therapeutic are described in various references, such as described in commonly assigned US2008/0081064 (Anderson, et al.)

In some aspects, the macrolide particulates are associated with a polymeric matrix that can be placed or formed at a target location in the body. For example, the particulates can be entrained or entrapped within the polymeric matrix, associated with the surface of a polymeric matrix, or combinations thereof. The polymeric matrix can modulate release of the macrolide therapeutic by one or more modes of release modulation.

The polymeric matrix can be in the form of an in-situ formed polymeric matrix, or an implant. The polymeric matrix can also be associated with an implantable medical device, such as in the form of a coating on a surface of the device or a matrix within the device. The polymeric matrix can be biostable, biodegradable, or can have both biostable and biodegradable properties. The polymeric matrix can be formed from synthetic or natural polymers.

The macrolide particulates may be associated with a lipid coating that includes one or more fatty acids, such as described in US2012/0165786 (Chappa et al.). For example, the macrolide particulates may be present in a coating on a balloon and covered associated with a lipid coating having a melting or softening point greater than room temperature and less than body temperature of a subject. The lipid coating may protect the macrolide therapeutic during insertion of the balloon catheter in the body and promote its release at the delivery site. An exemplary coating includes a mixture of dodecanoic acid and oleic acid e.g., (at a 1:1 wt ratio) applied over the macrolide particulates.

The macrolide particulates can be associated with a medical device, such as in a polymeric matrix associated with the medical device. In some cases, a particulate-containing coating can be formed on the surface of a medical article that can be introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, the macrolide particulates are associated with a balloon catheter, such as associated with a polymeric coating on a portion, or all of, the balloon surface. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. The macrolide particulates may be associated with a balloon catheter device such as described in US2012/0004605 (Chappa) which includes a a sleeve having a plurality of openings disposed over a coating on the balloon surface, with the sleeve adapted to expand between a compressed state and an enlarged state and to return to the compressed state. The macrolide particulates may be associated with a balloon catheter device such as described in US2012/0172839 (Chappa) which describes a catheter assembly with inner and outer expandable structures, and a therapeutic composition therebetween, with outer expandable structure having openings and photolabile seal scissile coatings. The macrolide particulates may be associated with a balloon catheter device such as described in US2012/0083733 (Chappa) which describes a catheter assembly with expandable structure with guard bonded to an expandable structure having reservoirs containing coating with active agent.

Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion can be then fed over the guidewire until the balloon reaches the target location in the vessel. The balloon can be then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

The balloon can be formed from any material, or combination of materials, capable of expanding, and suitable for use within the body. The balloon can be made from an elastomer, which can be a thermoplastic polymer with elastic properties. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The balloon can be made of a single elastomeric material, or a combination of materials. The balloon can be manufactured by an extrusion process, so that the elastic portion can be a single layer of material, or co-extruded to form a multi-layered material.

The elastic portion can have a thickness suitable for the application and device described herein. For example, an exemplary thickness of an elastic portion can be in the range of about 0.005 mm to about 0.25 mm, or about 0.005 mm to about 0.1 mm, or about 0.005 mm to about 0.05 mm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon.

In some aspects, the balloon on which the macrolide particulates are associated with can be formed upon can be a macroscopically smooth, microporous, flexible, elastic tubular prosthetic device made from a substantially non-elastic woven fabric tube as described in U.S. Pat. No. 4,652,263. The exterior of the tube can be an easily deformed, macroscopically smooth surface having a multiplicity of interstices, or apertures, among the threads and among the fibers of the threads.

In some embodiments, apertures in the balloon can have openings of predetermined sizes suitable for a biocompatible liquid to be released and to affect release of transfer of the macrolide particulates from the balloon surface. In some aspects the apertures have a size in the range of about 0.0025 mm to about 2.5 mm, about 0.005 mm to about 1 mm, or about 0.01 mm to about 0.5 mm. The apertures in the balloon can be of any shape or combination of shapes, although a preferred shape of the apertures can be round. Other shapes such as oval and polygonal (triangular, square, rectangular, hexagonal) shapes are contemplated.

The balloon on which a coating with macrolide particulates can be formed can be commercially obtained, for example, from Atrium Medical (e.g., the ClearWay™ RX catheter having a 0.014" guidewire, 6 & 7 Fr guide catheter, 1-4 ATM Infusion Pressure, and 134 cm catheter working length).

The balloon can be inflated using a fluid, which can be injected through an inflation port. The mechanics of fluid transfer and introduction within balloons vary according to the specific design of the catheter, and are well know in the art.

A balloon catheter with the inventive microparticulate-associated surface of the disclosure can be used in a balloon angioplasty procedure. Balloon angioplasty can be carried out for the treatment of diseased arteries to reduce atherosclerotic stenosis or to recanalize occluded arteries. In such a procedure, obstructed intraluminal passages are reopened or dilated by inflation of the balloon at the occluded site. According to the disclosure, balloon catheter having a microparticulate associated balloon portion can be inserted percutaneously into a luminal passage of a patient, such as an artery, vein, or airway. Once inserted, the balloon can be advanced to the desired treatment site, where the balloon can be inflated to dilate the luminal passage.

In some modes of practice, upon inflation of the balloon, at least a portion of the microparticulates that are associated with the surface of the balloon are transferred to the tissue of lumenal arterial wall at the target site.

For example, in aspects wherein the microparticulates are included in an expandable coating on the surface of the balloon, the inflation of the balloon can stretch the coating. The coating on the surface of the balloon can undergo physical changes that promote the release of the macrolide particulates. Upon insertion in a subject, a coating that is in the form of a flexible hydrogel matrix can become more hydrated, resulting in a loosening of the matrix material around the macrolide particulates. Also, the stretching of the coating (upon balloon expansion) can cause it to effectively become thinner than the coating on the balloon in an unexpanded state. In addition, the stretching of the coating can create pores in the coating from which the macrolide particulates can escape. The hydration, thinning of the coating and/or the creation of the pores can effectively cause the macrolide particulates to "pop out" of the coating upon balloon expansion.

In some modes of practice, macrolide particulates that are transferred can adhere to the arterial tissue at the target site. Accordingly, the macrolide particulates can release macrolide therapeutic at the target site, which can have a therapeutic effect on the tissue. The macrolide therapeutic at the target site can be useful to control tissue response after balloon dilation. For example, the macrolide particulates can release sirolimus that can inhibit neointimal proliferation at the dilated site.

In some modes of treatment, macrolide particulates can be used to macrolide therapeutic at a target site in a sustained profile. A polymeric material, such as a polymeric matrix in the form of a coating or shell on the particulates, or in the form of a matrix in which the particulates are embedded can modulate release over a longer and therapeutically useful time period.

Macrolide therapeutic released from the particulates can be used to treat specific diseases. For example, non-antibiotic macrolide particles can be used in various medical methods such as providing immunosuppressant activity to prevent rejection in organ transplantation. Non-antibiotic macrolides, such as rapamycin, can also be used to prevent hyperplasia and restenosis otherwise associated with inflammation, fibrosis, and thrombosis in tissues responses.

Antibiotic macrolide particles can be used to treat bacterial infections. For example, treatment can be carried out to reduce infection caused by gram-positive bacteria such as *Streptococcus pneumoniae* and *Haemophilus influenzae*, which may soft-tissue and the respiratory tract. Antibiotic macrolides can be used to treat infections caused by organisms such as Chlamydia, enterococci, *Legionella pneumophila, mycoplasma*, mycobacteria, *rickettsia*, pneumococci, streptococci, and staphylococci.

Example 1

Preparation of Rapamycin Nanospheres with Tween20™

Figure 4A:
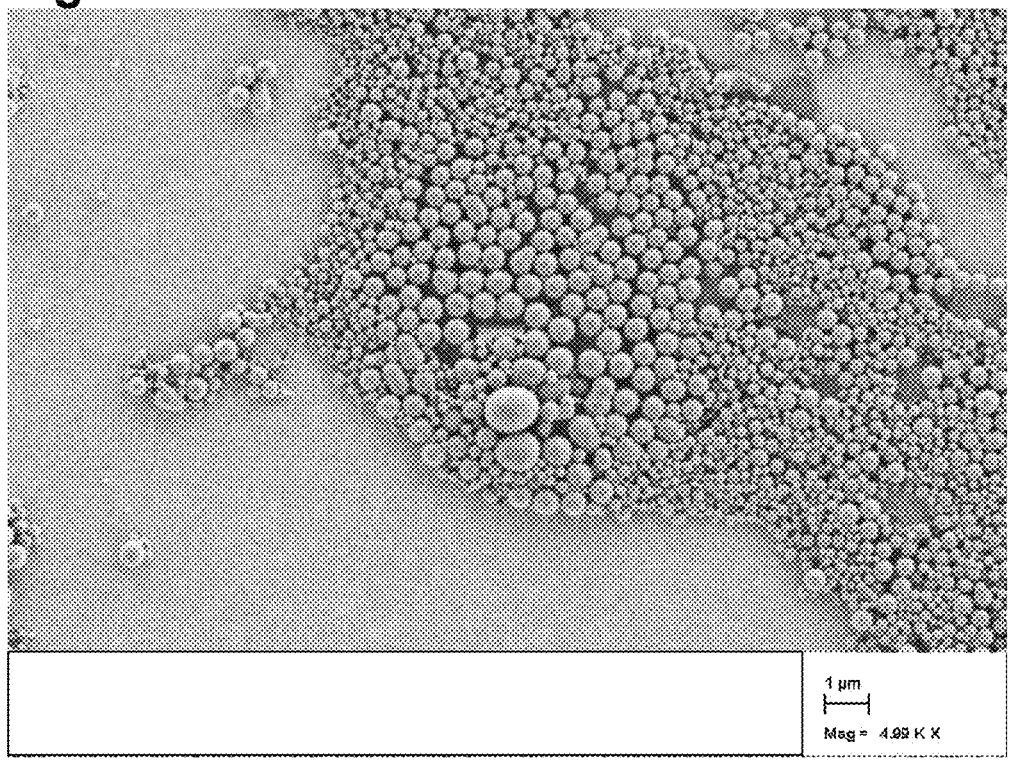
FIG. 4a is an electron micrograph of rapamycin nanospheres prepared by adding an aqueous Tween solution to a rapamycin/ethanol solution, observed following mixing/vortexing.

Rapamycin (available from (LC Laboratories; Woburn, Mass.) was dissolved in ethanol at 50 mg/mL. A second solution of a Tween™ 20 (available from Sigma Aldrich, St. Louis, Mo.; 50 µg/mL aq.) was prepared. While mixing/vortexing the rapamycin/ethanol solution the second Tween™ aqueous solution aqueous was added to the rapamycin solution until a ratio of ethanol/water 1:20 v/v was reached and the mixture stirred for an additional 5 minutes. FIG. 4a is an electron micrograph of the rapamycin nanospheres observable following mixing/vortexing.

Figure 4B:
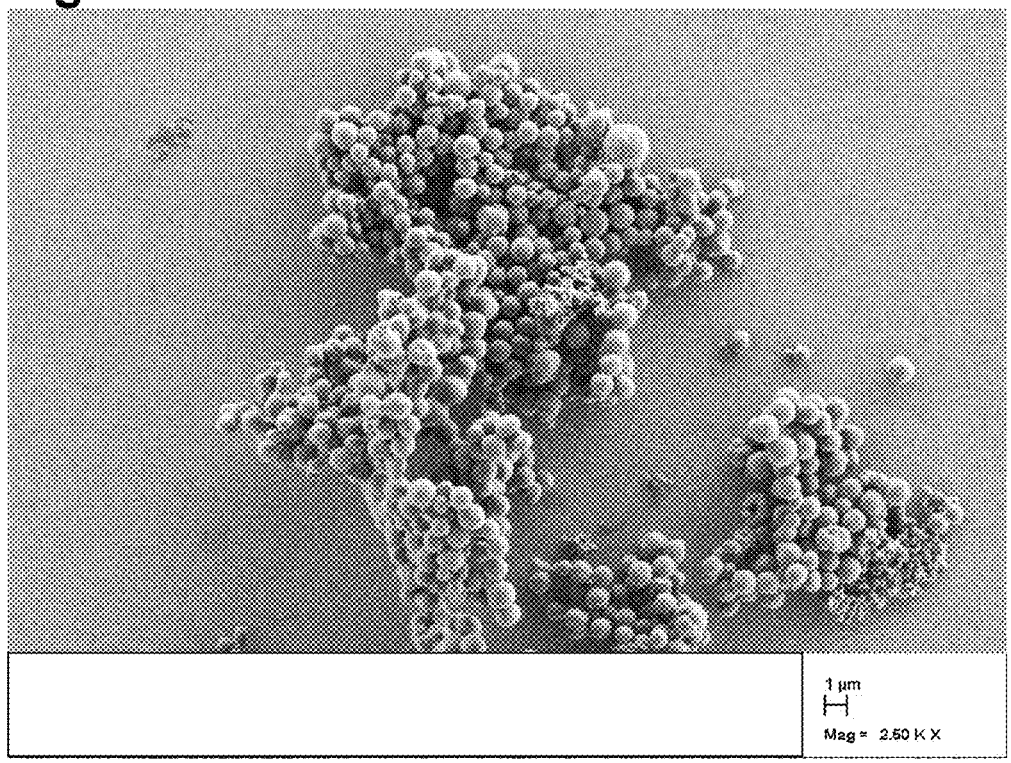
FIG. 4b is an electron micrograph of the rapamycin nanospheres prepared by adding an aqueous Tween solution to a rapamycin/ethanol solution, observed after lyophilization.

The mixture was frozen at −80° C., and then lyophilized in a benchtop lyophilizer (Freezone™ 2.5, LABCONCO) at 0.040 mbar, overnight. FIG. 4b is an electron micrograph of the rapamycin nanospheres after lyophilization. The mixture was then stored in an amber glass vial at room temperature for 2 weeks.

Figure 4C:
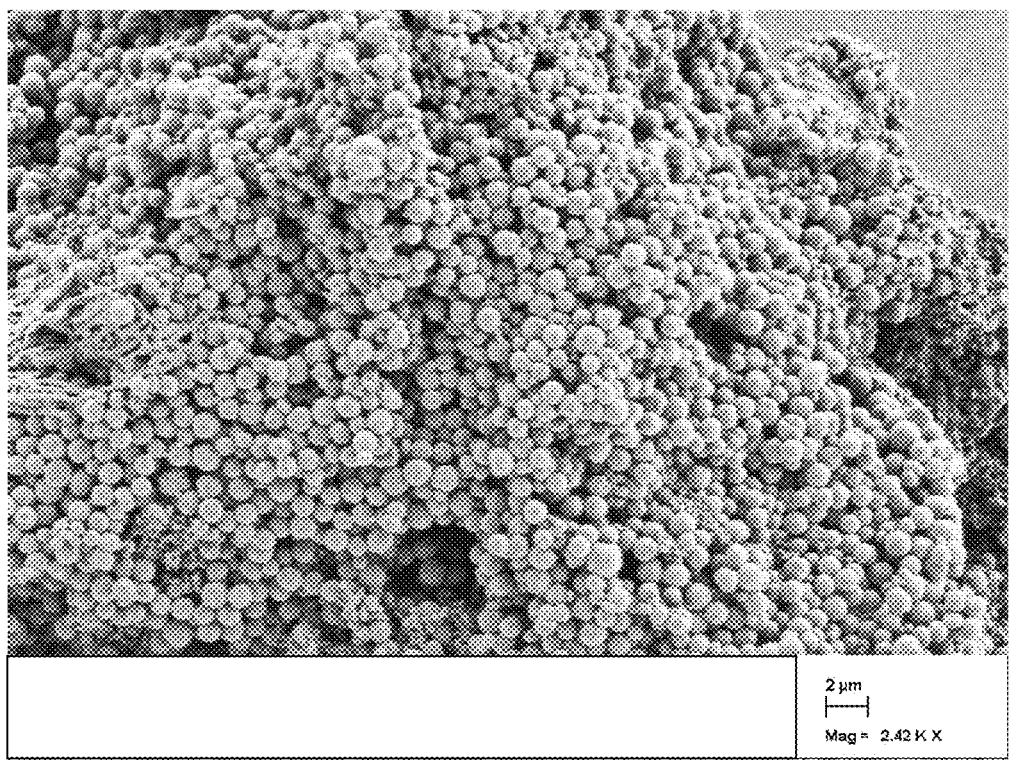
FIG. 4c is an electron micrograph of the rapamycin nanospheres prepared by adding an aqueous Tween solution to a rapamycin/ethanol solution, observed after two weeks storage and resuspension.

After two weeks of storage at ambient temperature, the lyophilized powder was resuspended in water with vortexing to form a fine suspension. FIG. 4C is an electron micrograph of the rapamycin nanospheres after two weeks storage and resuspension.

Example 2

Preparation of Rapamycin Nanospheres with CTAB

The process of Example 1 was repeated for the preparation of rapamycin nanospheres, but substituting cetyltrimethylammonium bromide at 50 µg/mL (CTAB; available from Sigma Aldrich) for Tween™ 20. Rapamycin nanospheres having properties similar to those formed using Tween™ 20 were obtained.

Example 3

Preparation of Rapamycin Nanospheres with Poly(Ethyleneimine) (PEI)

The process of Example 1 was repeated for the preparation of rapamycin nanospheres, but substituting poly(ethyleneimine) at 50 µg/mL (70 kDa; LC Laboratories) for Tween20™. Rapamycin nanospheres having properties similar to those formed using Tween™ 20 were obtained.

Example 4

Preparation of Rapamycin Nanospheres with α-Tocopherol

Figure 5:
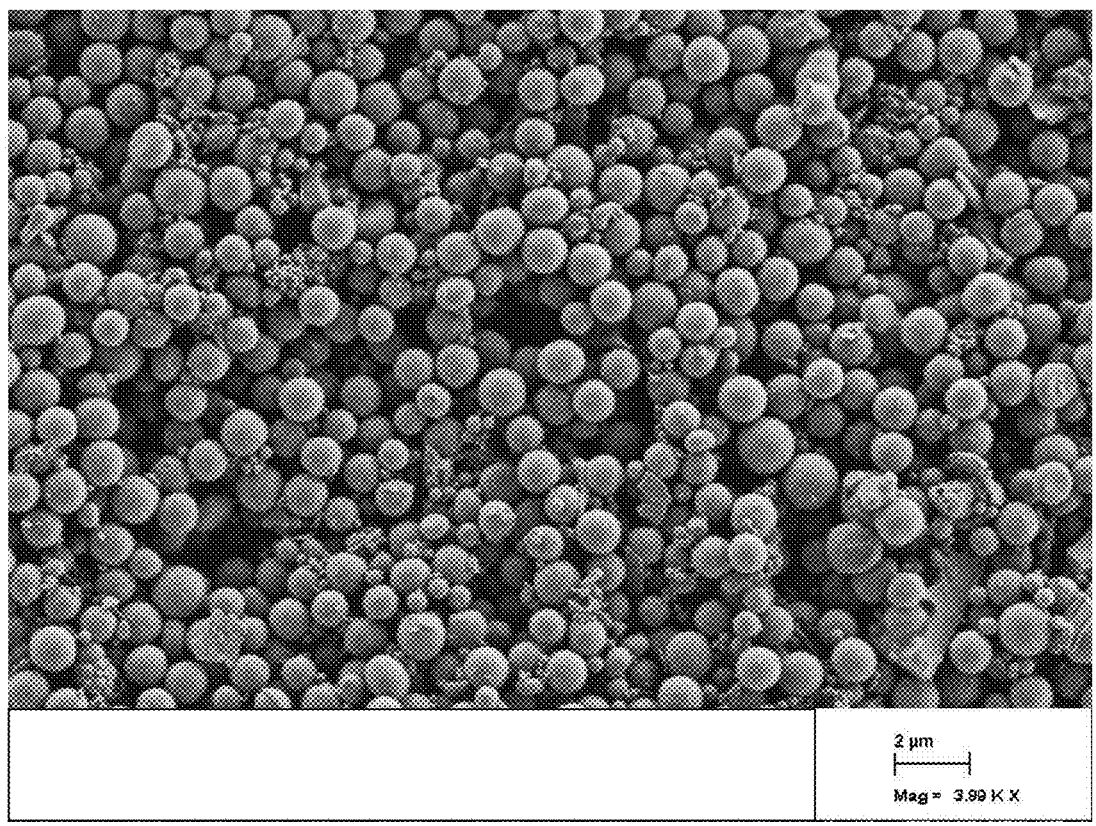
FIG. 5 is an electron micrograph of rapamycin particulates prepared by adding water to a rapamycin/α-tocopherol/ethanol solution.

Rapamycin was dissolved in ethanol at 50 mg/mL. Alpha (α)-tocopherol was dissolved in ethanol at 50 mg/mL and added at 0.5% w/w rapamycin. DI water was slowly added to the rapamycin solution while vortexing. Once precipitation occurred, as seen by a sudden change to a white milky suspension, more water was added quickly until a solvent-water ratio was reached of 1:20 ethanol:water (v/v), respectively. The mixture was then lyophilized as described above. FIG. 5 is an electron micrograph of the rapamycin nanospheres observable following mixing/vortexing.

Example 5

Preparation of Rapamycin Nanospheres with α-Tocopherol

Example 4 was repeated as described above, instead using rapamycin dissolved in ethanol at 40 mg/mL (in place of rapamycin dissolved in ethanol at 50 mg/mL). SEM analysis showed uniform spherical nanoparticles of average of about 450 nm in size

Example 6

Preparation of Rapamycin Nanospheres with Poly(Ethyleneimine) (PEI)

Example 5 was repeated as described above, instead a 50 μg/mL PEI 70 kDa (pH=7) aqueous solution was added slowly to the rapamycin solution in ethanol (in place of α-tocopherol). The resulting rapamycin nanospheres did not have the same degree of homogeneity as observed when prepared with the α-tocopherol as described in Examples 4 and 5.

Example 7

Balloon Coating with Rapamycin Nanospheres and PEI

Figure 6A:
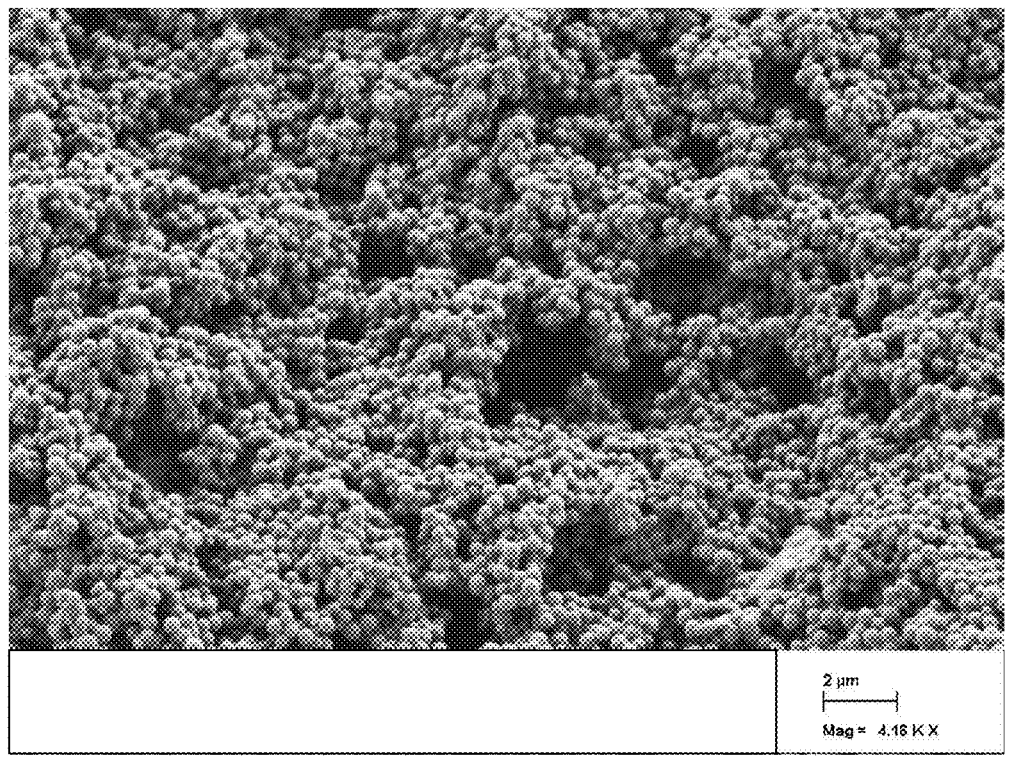
FIGS. 6a and 6b are electron micrographs of rapamycin particulates prepared by adding aqueous PEI solution to a rapamycin/ethanol solution, coated on a balloon surface.
Figure 6B:
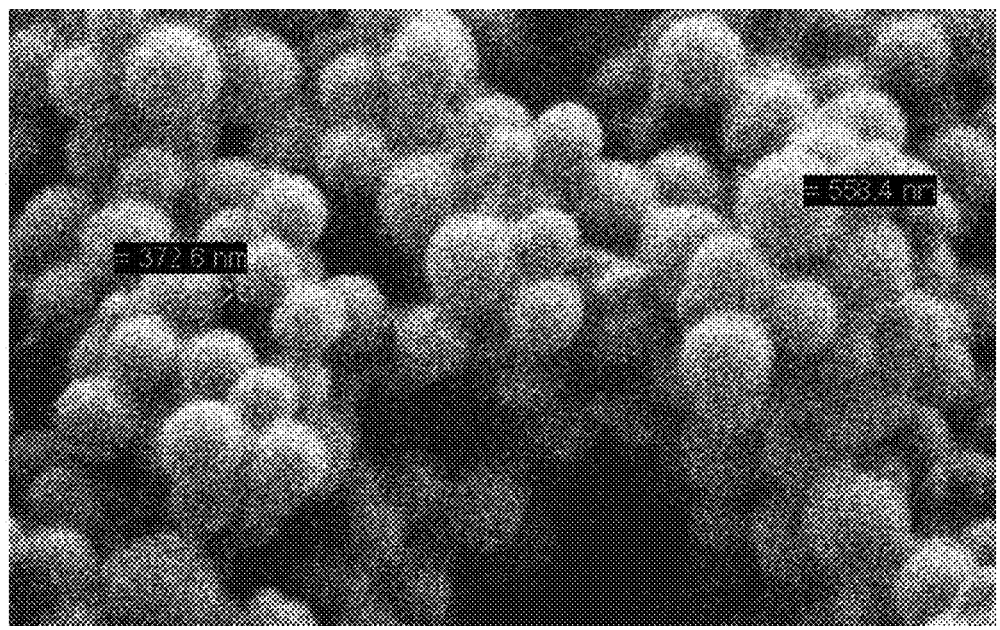

Rapamycin nanospheres are prepared in Example 3 were coated on a balloon surface. The coating ratio of rapamycin to PEI was 83:17 and was applied to the balloon surface as described in U.S. Patent Application Ser. No. 61/820,223, which is incorporated by reference in its entirety. The particle coated surface of the balloon is shown in FIGS. 6a and 6b.

Example 8

Balloon Coating with Rapamycin Nanospheres

Figure 7:
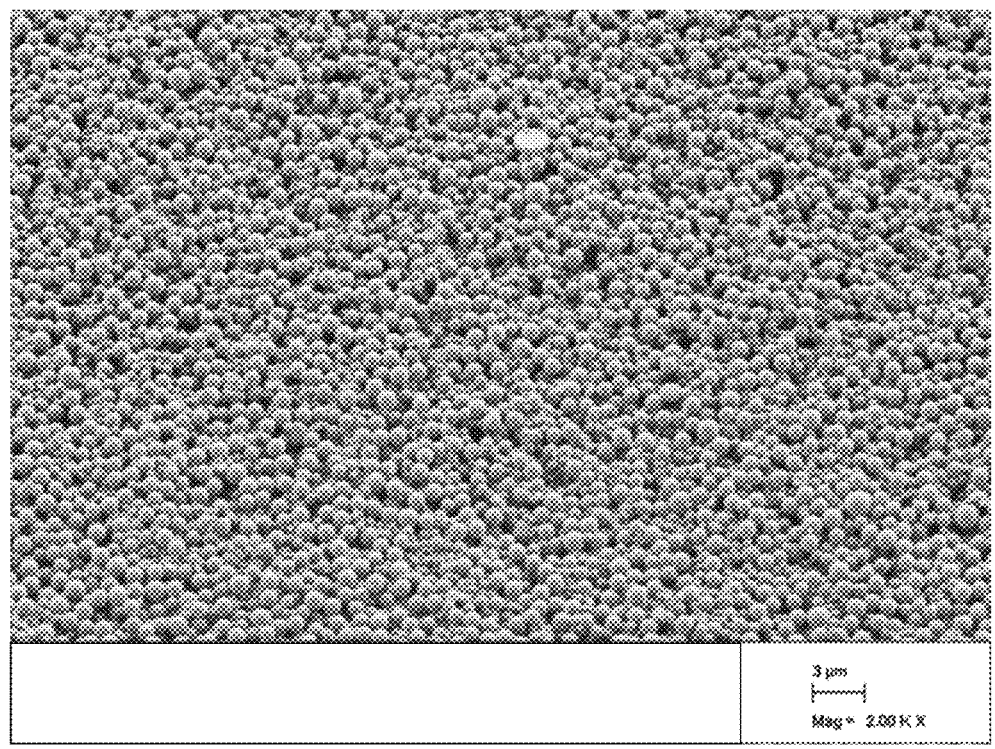
FIG. 7 is an electron micrograph of rapamycin particulates prepared by adding water to a rapamycin/α-tocopherol/ethanol solution, coated on a balloon surface.

Rapamycin nanospheres are prepared in Example 4 were coated on a balloon surface as described in Example 7. The particle coated surface of the balloon is shown in FIG. 7.

Example 9 (Comparative)

Preparation of Rapamycin Particulates with PVP-co-pNVA

The process of Example 1 was repeated, but substituting of poly(vinyl) pyrrolidone[50%]-co-(polyvinylformamide[50%])(PVP-co-pNVF) for Tween20™.

Poly(vinyl alcohol)-co-(polyvinylformamide); (PVP-co-pNVF) was prepared according to the following process:

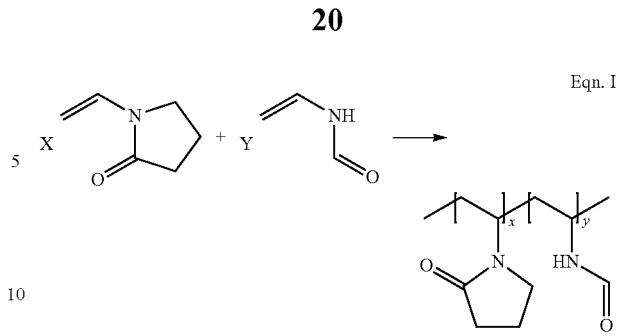

Eqn. I (x and y are each in the range of about 50 mole %). Deionized water (72.2 g), N-vinylformamide (NVF, 5.85 g; available from Sigma Aldrich, Milwaukee, Wis.), N-vinylpyrrolidone (NVP, 9.14 g; available from Sigma Aldrich), and 2,2'-Azobis(2-methylpropionamidine) dihydrochloride (Vazo 56WSP; 0.192 g; available from Sigma-Aldrich) were placed in a 100 ml bottle with screw top cap. The solution was sparged with nitrogen for 10 minutes. The jar was capped and the solution was rotated in an oven at 55° C. overnight. A portion of the ensuing aqueous solution (~6.7%) was placed in dialysis tubing (MWCO 12-14 kDa; SPECTRA/POR® available from VWR, Radnor, Pa.) and dialyzed against water for 3 days. The dialyzed solution was lyophilized following 5 stages at the temperatures, pressures and times listed below:

|  | Stages | | | | |
| --- | --- | --- | --- | --- | --- |
|  | 1 | 2 | 3 | 4 | final |
| Temperature (° C.) | −10 | 0 | 10 | 25 | 25 |
| Pressure (milltorr) | 400 | 200 | 100 | 50 | <20 |
| Time (hours) | 3 | 3 | 3 | 3 | >5* |

A white solid ((PVP-co-pNVF) polymer; 0.92 g) resulted. Hydrolysis of 1-vinyl-2-pyrrolidinone (NVP) and N-vinylformamide (NVF)

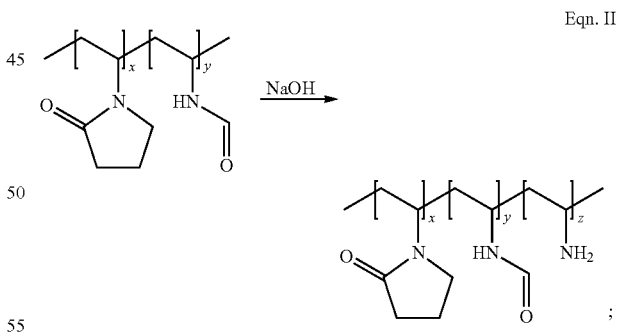

Eqn. II (wherein x, y and z are in the range of about 1-100%, with x+y+z=100%). (PVP-co-pNVF) polymer was hydrolyzed to yield co-polymers of poly(vinyl alcohol)-co-(polyvinylamine); Eqn. 1. The polymer solution of poly(vinyl alcohol)-co-(polyvinylformamide) was diluted with water, treated with NaOH, and refluxed for at least 20 hours. The hydrolyzed polymer solution was difiltered using a 10 kDa membrane (0.10 m² pellicon mini cassette; available from Millipore; Billerica, Mass.) until the pH was less than 7, which required about 15 to 20 liters of permeate. The difiltered solution was lyophilized as described above.

Using PVP-co-pNVF resulted in fusing of the nanospheres to form bigger aggregates which could not be easily dispersed upon aging.

Example 10 (Comparative)

Preparation of Rapamycin Particulates with Water

Figure 8:
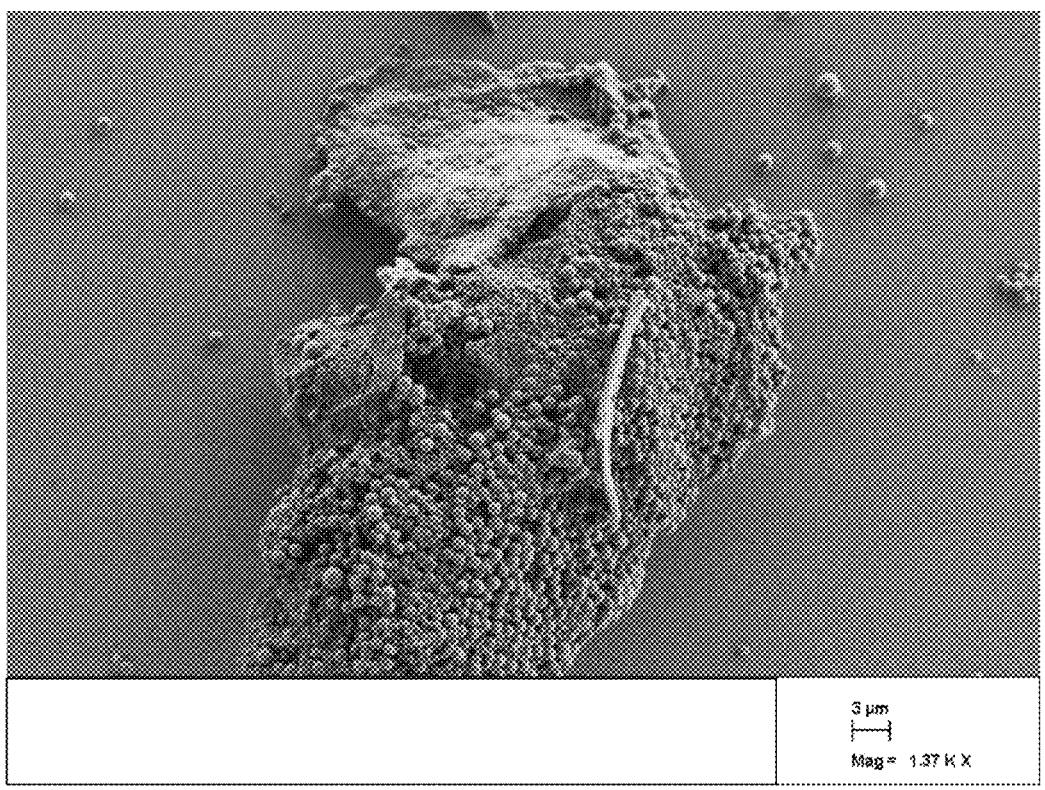
FIG. 8 is an electron micrograph of inhomogenous rapamycin particles prepared by adding water to a rapamycin/ethanol solution.

The process of Example 1 was repeated, without using Tween20™, so the composition added to the rapamycin/ethanol was only water. This yielded inhomogeneous particles as shown in FIG. 8.

What is claimed is:

1. A macrolide particulate comprising macrolide therapeutic agent in an amount of 95% or greater of the weight of the particulate, a component selected from the group consisting of poly(alkyleneimines), alkylated quaternary ammonium salts, and alkyl-substituted chromanols, and having a spherical or substantially spherical shape and a diameter in the range 0.1 μm to 10 μm.

2. The macrolide particulate of claim 1 further comprising a plurality of macrolide particulates comprising a particulate set.

3. An implantable or insertable medical device comprising a macrolide particulate according to claim 1.

4. The implantable or insertable medical device of claim 3 which is a balloon catheter.

5. The implantable or insertable medical device of claim 4 wherein the balloon catheter comprises a polymeric coating and the macrolide particulates are associated with the coating.

6. An injectable therapeutic composition comprising a macrolide particulate according to claim 1.

7. The macrolide particulate of claim 1, wherein the macrolide is rapamycin.

8. The macrolide particulate of claim 1, wherein the component is a poly(alkyleneimine).

9. The macrolide particulate of claim 1, wherein the component is an alkyl-substituted chromanol of Formula I:

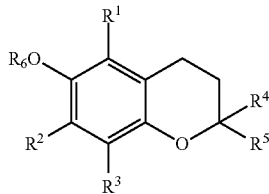

wherein $R^1$, $R^2$, $R^3$, and $R^4$ are independently selected from the group consisting of methyl ($-CH_3$) and hydrogen ($-H$); $R^5$ is a saturated or partially saturated, linear or branched C4-C16 alkyl group; $R^6$ is selected from the group consisting of H, $-C(O)R^7$, and $-R^8(CH_2CH_2O)_nH$, wherein $R^7$ is C1-C6 alkyl, and $R^8$ is a covalent bond (–) or a spacer group optionally containing one or more heteroatoms.

10. The macrolide particulate of claim 9 wherein the alkyl-substituted chromanol is selected from the group consisting of alpha (α) tocopherol, beta (β) tocopherol, gamma (γ) tocopherol, and delta (δ) tocopherol.

11. The macrolide particulate of claim 1 wherein the poly(alkyleneimine), alkylated quaternary ammonium salt, or alkyl-substituted chromanol, is present in an amount in the range of 0.01% to 5% of the weight of the particulate.

12. The macrolide particulate of claim 1 which is prepared by a method comprising steps of:
providing a first composition comprising the macrolide therapeutic agent and the alkyl-substituted chromanol dissolved in a liquid selected from the group consisting of C1-C4 alcohols,
forming a mixture by adding to the first composition a second composition that is aqueous, where mixing comprises agitating the mixture to cause the formation of macrolide particulates.

13. The macrolide particulate of claim 1 which is prepared by a method comprising steps of
providing a first composition comprising a macrolide therapeutic agent dissolved in ethanol at a concentration in the range of 10 mg/mL to 100 mg/mL,
forming a mixture by adding to the first composition a second composition that is a non-solvent for the macrolide therapeutic and comprises a component selected from the group consisting of poly(ethyleneimines), and alkylated quaternary ammonium salts, where mixing comprises agitating the mixture to cause the formation of macrolide particulates, where the second composition is added to the first composition at a ratio of at least 10:1 (vol:vol), respectively.

14. The macrolide particulate of claim 13 where in the step of forming the mixture the second composition is added to the first composition at a first rate until precipitation of the macrolide therapeutic agent, and then the second composition is added to the first composition at a second rate, with the second rate being greater than the first rate.

* * * * *